United States Patent [19]

Paust et al.

[11] 4,009,202

[45] Feb. 22, 1977

[54] 2(OR 3)-METHYL-1-ACETOXY-4-ALKOXY (OR PHENOXY)-1,3-BUTADIENES

[75] Inventors: Joachim Paust, Neuhofen; Horst Schumacher, Bobenheim, both of Germany

[73] Assignee: Badische Anilin- & Soda-Fabrik Aktiengesellschaft, Ludwigshafen (Rhine), Germany

[22] Filed: May 25, 1973

[21] Appl. No.: 363,861

[30] Foreign Application Priority Data

May 26, 1972 Germany .......................... 2225612
Feb. 28, 1973 Germany .......................... 2309885

[52] U.S. Cl. .................... 260/488 CD; 260/488 H; 260/491; 260/494; 260/598; 260/600 R; 260/602
[51] Int. Cl.$^2$ ........................................ C07C 69/145
[58] Field of Search ............... 260/488 H, 48.8 CD, 260/613 D, 615 R

[56] References Cited

UNITED STATES PATENTS 3,201,456  8/1965  Terry .............................. 260/488 H

OTHER PUBLICATIONS

Chem. Abstracts, 47:1575f.

*Primary Examiner*—Vivian Garner
*Attorney, Agent, or Firm*—Johnston, Keil, Thompson & Shurtleff

[57] ABSTRACT

2(or 3)-Methyl-1-acetoxy-4-alkoxy(or phenoxy)-1,3-butadienes and a process for their manufacture. The new 2(or 3)-methyl-1-acetoxy-4-alkoxy(or phenoxy)-1,3-butadienes are obtained by heating the corresponding methyl-4-alkoxy(or phenoxy)-crotonaldehyde with an excess of acetic anhydride and an alkali metal acetate, alkali metal carbonate or alkali metal hydroxide or a non-aromatic bicyclic amine or by heating the corresponding methyl-1-acetoxy-4,4-dialkoxy-2-butene in the presence of p-toluenesulfonic acid and quinoline at a temperature of from 150° to 260° C. The new compounds are of very considerable importance as intermediates in the synthesis of carotenoids.

7 Claims, No Drawings

2(OR 3)-METHYL-1-ACETOXY-4-ALKOXY (OR PHENOXY)-1,3-BUTADIENES

The present invention relates to 2(or 3)-methyl-1-acetoxy-4-alkoxy(or phenoxy)-1,3-butadienes and their production from 2(or 3)-methyl-4-alkoxy(or phenoxy)-crotonaldehyde or from 2(or 3)-methyl-1-acetoxy-4,4-dialkoxy-2-butene.

The new compounds are of very considerable importance as intermediates in the synthesis of carotenoids. For example retinal, which has hitherto only been obtainable by a complicated process, can be prepared in a simple way in a single vessel by reacting 2-methyl-1-acetoxy-4-methoxy-1,3-butadiene with chlorine or bromine at temperatures below 10° C and then adding an alcoholic solution of an alkali metal alcoholate and a β-ionylidene-ethyltriphenylphosphonium salt to the reaction mixture. This elegant method of synthesizing retinal using the compounds of this invention is described in Example 20. Retinal has practically the same effect as vitamin A while being more stable to acids and oxidation. Furthermore, retinal is of great significance as an immediate precursor of β-carotene which is of great importance as a foodstuff dye and as a provitamin A.

Reaction of 3-methyl-1-acetoxy-4-methoxy-1,3-butadiene with chlorine or bromine at temperatures below 10° C followed by adding an alcoholic solution of an alkali metal alcoholate and a retinyltriphenylphosphonium salt gives, in an elegant way and in a single reactor, β-apo-$C_{25}$-carotenal which is of great importance as a foodstuff dye and as a provitamin A. A more detailed description of this synthesis is given in Example 21.

The new methyl-1-acetoxy-4-alkoxy(or phenoxy(-1,3-butadienes of the formula I

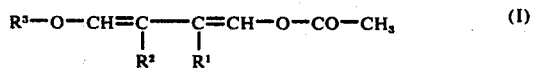

in which $R^1$ and $R^2$ are different and denote hydrogen or methyl and $R^3$ is an aliphatic hydrocarbon radical of from 1 to 4 carbon atoms or phenyl, can for example be prepared in a very advantageous manner by heating a methyl-4-alkoxy(or phenoxy)crotonaldehyde of the formula II

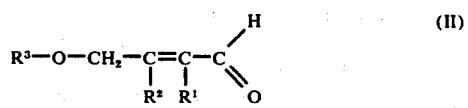

in which $R^1$, $R^2$ and $R^3$ have the meanings given above, with an excess of acetic anhydride and an alkali metal acetate, alkali metal carbonate or alkali metal hydroxide or a non-aromatic bicyclic amine at a temperature of from 100° to 150° C, preferably at reflux temperature.

The 4-alkoxymethylcrotonaldehydes of the formula II which are required as starting materials for this process can be prepared for example in the following simple manner:

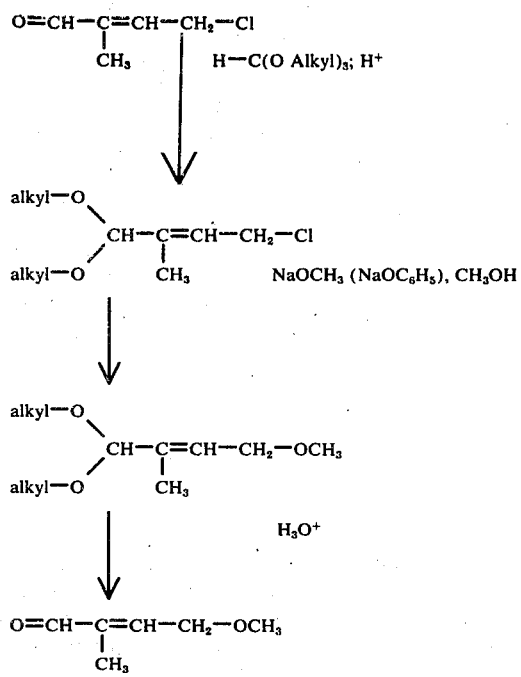

Examples of suitable starting materials are 2-methyl-4-methoxybut-2-en-1-al, 2-methyl-4-ethoxybut-2-en-1-al, 2methyl-4-isopropoxybut-2-en-1-al, 2-methyl-4-phenoxybut-2-en-1-al, 3-methyl-4-methoxybut-2-en-1-al and 3-methyl-4-ethoxybut-2-en-1-al.

In order to convert these 4-alkoxymethylcrotonaldehydes of the formula II into the butadienediol derivatives of the formula I they are heated to boiling with stirring and under reflux with an excess of acetic anhydride and an alkali metal acetate, carbonate or hydroxide or a bicyclic amine.

Acetic anhydride is used in an amount of from 1 to 7 moles, preferably 2 to 3 moles, per mole of starting compound.

Preferred alkali metal acetates, carbonates and hydroxides are sodium acetate, potassium acetate, potassium carbonate and potassium hydroxide. The alkali metal acetates, carbonates and hydroxides are usually used in amounts of from 0.3 to 3 moles per mole of starting compound, depending on the type of alkali metal compound used. If for example potassium carbonate is employed 0.5 mole per mole of starting compound is sufficient, whereas in the event of potassium acetate being used it is advantageous to employ 2 to 3 moles per mole of starting compound.

If sodium acetate is used the period required for this reaction step is about 5 to 9 hours, whereas in the case of potassium acetate, potassium carbonate or potassium hydroxide the time required for achieving the same conversion is only 1 to 2 hours, preferably 60 to 80 minutes.

Examples of suitable non-aromatic bicyclic amines are 1,4-diazobicyclo-[2,2,2]-octane (DABCO) and 1,5-diazabicyclo-[4,3,0]-nonene-(5).

The usual amines such as ethylamine, triethylamine, pyridine and quinoline cannot be used in the reaction. The non-aromatic bicyclic amines are preferably used in amounts of from 0.5 to 2 moles per mole of starting compound.

Processing of the reaction mixture is effected in a conventional manner, for example by stirring with a water-immiscible solvent, preferably diethyl ether or benzene, removing the alkali metal acetate by filtration or by washing the mixture with water followed by fractional distillation of the organic phase or simply by adding water and separating and fractionating the upper phase. The 2(or 3)-methyl-1-acetoxy-4-alkoxy-(or phenoxy)-1,3-butadienes are obtained as a mixture of substantially two geometric isomers.

This process is illustrated by Examples 1 to 7.

We have also found that the methyl-1-acetoxy-4-alkoxy-1,3-butadienes of the formula I can advantageously be prepared by heating methyl-1-acetoxy-4,4-dialkoxy-2-butenes of the formula III

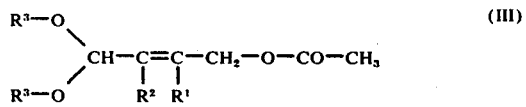  (III)

in which $R^1$ and $R^2$ have the meanings given above and $R^3$ denotes an aliphatic hydrocarbon radical of from 1 to 4 carbon atoms, in the presence of p-toluenesulfonic acid and quinoline at a temperature of from 150° to 260° C, preferably 175° to 210° C.

It is surprising that the compounds of the formula I are obtained in good yields under the said reaction conditions since they are enol esters which usually are rapidly decomposed by transesterification at such high temperatures in the presence of acids and/or basic catalysts and alcohols ($R^3OH$).

The 2(or 3)-methyl-1-acetoxy-4,4-dialkoxy-2-butenes required as starting materials for this process can be prepared in a simple way by acetalizing the corresponding methylacetoxy-2-butenals. The 3(or 2)-methyl-4-acetoxy-2-buten-1-als may be prepared for example by reacting ω-chlorotiglaldehyde or ω-bromotiglaldehyde with an alkali metal acetate or an alkaline-earth metal acetate (cf. German Pat. No. 1,227,000) or by rearrangement of 2-formyl-2-hydroxybut-3-ene or its acetate in the presence of copper compounds (cf. German Pat. No. 1,297,597). Acetalization of the 3(or 2)-methyl-4-acetoxy-2-buten-1-als is carried out in a conventional manner by reacting the butenals with an alcohol in the presence of an equimolar amount of the corresponding ortho ester using an acid catalyst.

The process of the invention is advantageously carried out by adding p-toluenesulfonic acid and quinoline to the reaction mixture obtained in the acetalization of the 3(or 2)-methyl-4-acetoxy-2-buten-1-als with a lower alcohol and heating the whole to the reaction temperature.

When using the reaction mixture obtained in the acetalization as starting material for the process of the invention it is advantageous to catalyze the acetalization with p-toluenesulfonic acid as well.

In accordance with this invention p-toluenesulfonic acid is used in an amount of from 0.5 to 4 mole% and quinoline in an amount of from 2 to 20 mole%, based on starting compound III.

The reaction temperature is 150° to 260° C, preferably 175° to 210° C.

The reaction may be carried out at atmospheric or subatmospheric pressure. If subatmospheric pressure is used, care should be taken to ensure that the starting compounds (2(or 3)-methyl-4-acetoxy-2-butenaldialkylacetals) are not volatile at the reaction temperature required.

The reaction time is usually from 10 to 30 minutes.

This process is illustrated by Examples 8 to 10.

It is also possible to carry out the reaction of the methyl-acetoxy-4,4-dialkoxy-2-butenes to form the 1,3-butadienes (I) of the invention in the presence of other weakly acid catalysts, e.g. silica gel, aluminum oxide powder (acidic), sodium dihydrogen phosphate, ammonium dihydrogen phosphate or potassium bisulfate, but the best results are obtained when using p-toluenesulfonic acid and quinoline.

We have also found that the new 2(or 3)-methyl-1-acetoxy-4-alkoxy(or phenoxy)-1,3-butadienes I can be used with particular advantage for the production of methylfumaraldehydemonoacetals of the formula IV

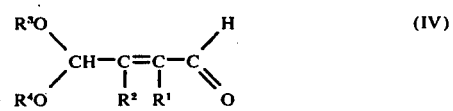  (IV)

in which $R^1$ and $R^2$ have the meanings given above and $R^3$ and $R^4$ are identical or different and each denotes an aliphatic hydrocarbon radical of from 1 to 4 carbon atoms and $R^3$ may also be phenyl. The methylfumardialdehydemonoacetals of the formula IV are also compounds which are of very great importance as intermediates in the synthesis of carotenoids.

For the preparation of the methylfumaraldehydemonoacetals a butadienediol derivative of the formula I is dissolved in a solvent, then chlorine or bromine is gradually added to the solution with stirring, intense cooling and exclusion of moisture, a solution of a strong base in a lower alcohol is added to the reaction mixture and the whole is allowed to react for from 10 minutes to 2 hours at a temperature of from −50° to +50° C, preferably at −10° to +25° C, particularly at room temperature, while stirring. Examples of solvents suitable for this reaction are saturated hydrocarbons such as n-pentane and cyclohexane, halogenated hydrocarbons such as methylene chloride and carbon tetrachloride, ethers such as diethyl ether, dimethyl ether and tetrahydrofuran, and preferably lower alcohols, i.e. alcohols having 1 to 4 carbon atoms, particularly methanol.

If halogenation is carried out in a lower alcohol as solvent, it is possible to add to the reaction mixture an aqueous solution of a strong base, e.g. an aqueous alkali metal hydroxide solution, instead of a solution of a strong base in a lower alcohol.

0.1 to 3 molar, preferably 0.5 to 1.4 molar, solutions of the butadienediol derivatives are used.

Chlorine or bromine are added to the reaction mixture in gaseous form or advantageously in the form of concentrated solutions in carbon tetrachloride. The halogen may be added at the same rate at which the heat of reaction can be removed. The halogen is used in an amount of from 1 to 1.1 moles per mole of butadienediol derivative. Halogenation is effected at temperatures of from room temperature to −70° C, preferably 0° to −50° C.

If halogenation is carried out in an alcohol as solvent, it is advantageous, especially at temperatures above −30° C, to add to the reaction mixture a small amount of a weak base, such as pyridine, sodium acetate and trialkylamines, in order to prevent the formation of a second acetal grouping.

When halogenation has been completed, a solution of a strong base in a lower alcohol or in water is added to the reaction mixture.

Examples of strong bases suitable for the purposes of this invention are alkali metal alcoholates, alkaline-earth metal alcoholates and alkali metal phenolates and, in the event of halogenation being carried out in alcoholic solution, additionally alkali metal hydroxides, preferably sodium hydroxide. It is particularly advantageous to use sodium alcoholates or potassium alcoholates, especially the alcoholate of the alcohol which is added to the reaction mixture. The strong bases are usually used in an amount of from 2 to 5 moles, preferably about 2.5 moles, per mole of butadienediol derivative of the formula I.

Processing of the reaction mixture is carried out in a conventional manner, e.g. by adding to the reaction mixture water and a solvent which is practically immiscible with water, such as chloroform, benzene and diethyl ether, and fractionating the organic phase separated.

The preparation of methylfumardialdehydemonoacetals is illustrated in Examples 11 to 19.

The processes of the invention have made it possible for the first time to prepare the 2(or 3)-methyl-1-acetoxy-4-alkoxy(or phenoxy)-1,3-butadienes of the formula I which are of great importance as intermediates for the synthesis of carotenoids. The processes are relatively easy to carry out and usually give good yields.

The invention is illustrated by the following Examples.

EXAMPLE 1 a. A mixture of 114 g (1 mole) of 2-methyl-4-methoxybut-2-en-1-al (4-methoxytiglaldehyde), 500 g of acetic anhydride and 196 g (2 moles) of anhydrous potassium acetate is heated under reflux in a 2-liter flask at about 135° C for 50 minutes while stirring. The reaction mixture is allowed to cool to room temperature and stirred with 700 ml of diethyl ether and the precipitated potassium acetate is filtered off. The filtrate is fractionated using a Vigreux column 20 cm in length. The fraction having a boiling point at 0.5 mm Hg of 50° to 65° C consists of a mixture of the cis-trans isomers of 1-acetoxy-2-methyl-4-methoxybuta-1,3-diene. The yield is 70% of the theory.

NMR ($\delta$[ppm], CDCl$_3$, TMS)

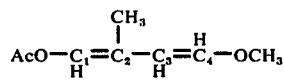

C$_1$-H 7,07 (S, 1H)
C$_4$-H 6,55 (d, 1H, J$_{AB}$ 13 Hz)
C$_3$-H 5,48 (d, 1H, J$_{AB}$ 13 Hz)
CH$_3$O- 3,58 (S, 3H)

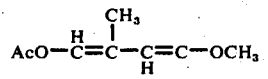

C$_1$-H 6,81 (S, 1H)
C$_3$-H 5,92 (d, 1H, J$_{AB}$ 13 Hz)
C$_4$-H 6,60 (d, 1H, J$_{AB}$ 13 Hz)

CH$_3$O- 3,63 (S, 3H)

b. The procedure of Example 1(a) is followed except that 164 g (2 moles) of anhydrous sodium acetate is used instead of 196 g of potassium acetate and the reaction mixture is heated at about 135° C for 8 hours instead of 50 minutes. 107 g of a mixture of cis-trans isomers of 1 acetoxy-2-methyl-4-methoxybuta-1,3-diene is obtained. The yield is 68% of the theory.

EXAMPLE 2

The procedure of Example 1 (a) is followed except that 128 g (1 mole) of 2-methyl-4-ethoxybut-2en-1al (4-ethoxytiglaldehyde) is used instead of 114 g of 2-methyl-4-methoxybut-2-en-1-al. There is obtained 126 g of a distillate having a boiling point at 0.6 mm Hg of 53° to 69° C and which, according to gas chromatographic and NMR spectroscopic investigation, consists of two cis-trans isomers of 1acetoxy-2-methyl-4-ethoxybuta-1,3-diene. The yield is 74% of the theory.

EXAMPLE 3

A mixture of 114 g of 2-methyl-4-methoxybut-2-en-1-al, 500 g of acetic anhydride and 112 g (1 mole) of 1,4-diazabicyclo- 2,2,2-octane (DABCO) is heated under reflux in a 2-liter flask at about 135° C for 1 hour while stirring. The reaction mixture is allowed to cool to room temperature, 600 ml of benzene is added and the whole is washed three times, each time with 500 ml of water. Fractionation of the organic phase gives 101 g of a fraction having a boiling point at 0.5 mm Hg of 50° to 65° C which, according to gas chromatographic and NMR spectroscopic investigation, consists of a mixture of three cis-trans isomers of 1-acetoxy-2-methyl-4-methoxybuta-1,3-diene. The yield is 62%.

EXAMPLE 4

A mixture of 71 g (0.5 mole) of 2-methyl-4-isopropoxybut-2-en-1-al, 250 g of acetic anhydride and 98 g (1 mole) of anhydrous potassium acetate is heated under reflux at about 135° C for 45 minutes while stirring. The reaction mixture is allowed to cool and stirred with 350 ml of diethyl ether, the precipitated potassium acetate is filtered off and the filtrate is fractionated. There is obtained 136 g of a fraction having a boiling point at 0.4 mm Hg of 55° to 56° C and which consists of 1-acetoxy-2-methyl-4-isopropoxybuta-1,3-diene. The yield is 74% of the theory.

EXAMPLE 5

A mixture of 176 g (1 mole) of 2-methyl-4-phenoxybut-2-en-1-al 500 g of acetic anhydride and 196 g (2 moles) of anhydrous potassium acetate is heated under reflux in a 2-liter flask at about 135° C while stirring. The reaction mixture is allowed to cool, 600 ml of benzene is added, the precipitated potassium acetate is filtered off and the filtrate is fractionated. There is obtained 186 g of a fraction having a boiling point at 0.3 mm Hg of 108° to 112° C and consisting of 1-acetoxy-2-methyl-4-phenoxybuta-1,3-diene. The yield is 85% of the theory.

EXAMPLE 6

A mixture of 114 g (1 mole) of 2-methyl-4-methoxybut-2-en-1-al, 200 g (2moles) of acetic anhydride and 69 g (0.5 mole) of anhydrous potassium carbonate is heated at reflux temperature (about 135° C) for about 1 hour with intense stirring. The reaction mixture is cooled to room temperature, water is added until the salts have been dissolved, the upper phase is separated, the aqueous phase is extracted with a small amount of benzene, and the two organic phases are combined and fractionated. There is obtained 132 g of a fraction having a boiling point at 0.8 mm Hg of 48° to 55° C and consisting of cis-trans-1-acetoxy-2-methyl-4-methoxy-1,3-butadiene. The yield is 85% of the theory.

EXAMPLE 7

A mixture of 114 g (1 mole) of 3-methyl-4-methoxybut-2-en-1-al, 500 g of acetic anhydride and 207 g (1.5 moles) of anhydrous potassium carbonate is heated under reflux at about 135° C while stirring. The reaction mixture is allowed to cool and then stirred with 700 ml of ether, the precipitated potassium salt is filtered off, the filtrate is concentrated in a rotational evaporator the residue is fractionated. 106 g of a fraction having a boiling point at 0.4 mm Hg of 48° to 55° C and consisting of cis-trans isomers of 1-acetoxy-3-methyl-4-methoxybuta-1,3-diene is obtained. The yield is 65% of the theory.

EXAMPLE 8

28.4 g (0.2 mole) of 2-methyl-4-acetoxy-2-butenal is dripped into a mixture of 23.3 g (0.22 mole) of o-formic acid methyl ester, 12.8 g (0.4 mole) of methanol and 0.35 g (2millimoles) of p-toluene-sulfonic acid. Acetalization takes place while the temperature rises. After 1 hour 2 g (15 millimoles) of quinoline is added and the whole is heated at 185° to 190° C (internal temperature) and at a pressure of 200 mm Hg for 20 minutes The methanol which is eliminated is distilled off in a 20-cm column. Then the pressure is adjusted to 20 mm Hg with the result that 23.2 g of 1-acetoxy-3-methyl-4-methoxy-1,3-butadiene in the form of a mixture of two geometric iosmers is obtained. The yield is 75% of the theory.

EXAMPLE 9

28.4 g (0.2 mole) of 3-methyl-4-acetoxy-2-butenal is converted, by a method analogous to that used in Example 8, into 1-acetoxy-2-methyl-4-methoxy-1,3-butadiene (boiling point at 0.5 mm Hg 50° to 65° C) via the dimethylacetal as intermediate. The yield is also 75% of the theory.

EXAMPLE 10

28.4 g (0.2 mole) of 2-methyl-4-acetoxy-2-butenal, 32.0 g (0.22 mole) of o-ethyl formate and 23 g (0.5 mole) of ethanol are reacted by adding a catalytic amount (about 2 millimoles) of p-toluenesulfonic acid to form the diethylacetal. After 1 hour 2 g (15 millimoles) of quinoline is added and the mixture is heated at 190° to 195° C at a pressure of 240 mm Hg for 25 minutes. Excess formate and ethanol are distilled off in a 20-cm column. Then the pressure is reduced to 20 mm Hg with the result that 22.1 g of 1-acetoxy-3-methyl-4-ethoxy-1,3-butadiene (boiling point at 20 mm Hg 102° to 110° C) is obtained in the form of a mixture of two geometric isomers. The yield is 65% of the theory.

Production of methylfumaraldehydemonoacetals (Examples 11 to 19)

EXAMPLE 11

15.6 g (0.1 mole) of 1-acetoxy-2-methyl-4-methoxy-1,3-butadiene is dissolved in 110 ml of methanol. After the addition of 18 g (0.22 mole) of anhydrous sodium acetate the whole is cooled to −30° C and then 0.1 mole of gaseous chlorine is introduced into the solution at the said temperature in the course of 15 minutes while stirring. Then 45 g (0.25 mole) of a 30% methanolic solution of sodium methylate is introduced without cooling being continued and then the whole is stirred for another 5 minutes at 0° C. After adding 500 ml of water, extraction is effected three times, each time with 100 ml of methylene chloride. The methylene chloride solution is washed twice, each time with 100 ml of water, and then dried with sodium sulfate. The solvent is distilled off using a rotational evaporator (room temperature, about 87 mm Hg) and the residue (16.5 g) is distilled at 0.3 mm Hg. There is obtained 12.2 g (85% of the theory) of trans-3-methyl-2-buten-1,4-dial-1-dimethyl-acetal having a boiling point at 0.3 mm Hg of 42° to 44° C.

EXAMPLE 12

15.6 g (0.1 mole) of 1-acetoxy-2-methyl-4-methoxy-1,3-butadiene and 17.4 g (0.22 mole) of pyridine are dissolved in 110 ml of methanol. 0.1 mole of chlorine is passed in at 0° C in the course of about 15 minutes and then 45 g of a 30% methanolic solution of sodium methylate (0.25 mole) is dripped in. When the sodium methylate is added the solution is temporarily colored deep violet. Processing is carried out as described in Example 11 and gives, after distillation, 12.2 g (85%) of trans-2-methyl-4,4-dimethoxy-2-butenal.

EXAMPLE 13

The procedure of Example 12 is followed except that 22 g (0.22 mole) of triethylamine is used instead of 17.4 g of pyridine. 11.7 g (81%) of trans-3-methyl-2-buten-1,4-dial-1-dimethylacetal is obtained.

EXAMPLE 14

15.0 g (0.1 mole) of 1-acetoxy-2-methyl-4-methoxy-1,3-butadiene and 18 g (0.22 mole) of anhydrous sodium acetate are dissolved in 100 ml of methanol. Then a solution of 16 g (0.1 mole) of bromine in 20 ml of methanol is dripped in at −30° C while stirring and subsequently, without cooling being continued, 45 g of a 30% methanolic solution of sodium methylate (0.25 mole) is dripped in. Processing is effected as described in Example 11. 10.8 g (75%) of trans-3-methyl-2-buten-1,4-dialdimethylacetal is obtained.

EXAMPLE 15

The procedure of Example 14, is followed except that 17.4 g (0.22 mole) of pyridine is used instead of sodium acetate. The yield of trans-3-methyl-2-buten-1,4-dialdimethylacetal is 11.3 g (79%).

EXAMPLE 16

15.6 g (0.1 mole) of 1acetoxy-2-methyl-4-methoxy-1,3-butadiene and 17.4 g (0.22 mole) of pyridine are dissolved in 110 ml of ethanol. 0.1 mole of chlorine is passed in at −50° C in the course of 15 minutes, then a solution of 5.6 g (0.25 mole) of sodium in 55 ml of ethanol is poured in and the temperature is allowed to rise to 0° C. Processing is carried out as described in Example 11. Upon distillation 12.5 g (80%) of 2-methyl-4-methoxy-4-ethoxy-2-butenal having a boiling point at 0.1 mm Hg of 48° to 50° C is obtained (solvent determines 4-alkoxy group).

EXAMPLE 17

10.7 ml (0.21 mole) of bromine is dripped into a solution of 31.2 g (0.2 mole) of 1acetoxy-2-methyl-4-methoxybuta-1,3-diene in 150 ml of ether while stirring, cooling with ice, gassing with nitrogen and excluding moisture. Care is taken to ensure that the temperature of the reaction mixture does not exceed 5° C.

Then a solution of 27 g (0.5 mole) of sodium methylate in 400 ml of methanol is added to the reaction mixture and the whole is stirred for 1 hour at room temperature in order to complete the reaction. The mixture is then concentrated to ⅖ of its volume, 500 ml of water is added and then extraction is carried out with a total of 600 ml of chloroform. After separating the organic phase, distilling off the solvent in a rotational evaporator and fractionating the residue in a high vacuum. 18.4 g of 3-methylfumaraldehyde-1-dimethylacetal (boiling point at 10 mm Hg 71° to 76° C) is obtained. The yield is 64% of the theory, based on 1-acetoxy-2-methyl-4-methoxybuta-1,3-diene.

EXAMPLE 18

The procedure of Example 17 is followed except that 150 ml of n-pentane is used instead of 150 ml of ether and cooling is effected with brine instead of with ice in order to ensure that the temperature does not rise above −20° C. 20.6 g of 3-methylfumaraldehyde-1-dimethylacetal having a boiling point at 0.2 mm Hg of 40° to 60° C is obtained. The yield is 71% of the theory.

EXAMPLE 19

The procedure of Example 17 is followed but ice cooling during bromination is replaced by cooling in a bath which cools the reaction mixture during bromination to −60° C. 20.2 g of 3-methylfumaraldehyde-1-dimethylacetal is obtained. The yield is 70% of the theory.

EXAMPLE 20

Production of retinal from 1-acetoxy-2-methyl-4-methoxy-1,3-butadiene 15.6 g (0.1 mole) of 1-acetoxy-2-methyl-4-methoxy-1,3-butadiene is dissolved in 100 ml of methanol. 18 g (0.22 mole) of anhydrous sodium acetate is added and the whole is cooled to −20° C. At this temperature 0.1 mole of chlorine is introduced and then 0.5 mole of sodium methylate (30% solution in methanol) and 0.1 mole of β-ionylidenethyltriphenylphosphonium bromide (30% solution in methanol) are dripped in. When the temperature of the mixture has risen to +10° C, the mixture is acidified with 10% aqueous sulfuric acid (about 200 ml), stirring is continued for 10 minutes at room temperature and then extraction is effected twice, each time with 100 ml of n-hexane. The hexane phase is washed with water and concentrated in vacuo in a rotational evaporator. The residue consists of a mixture of geometric isomers of retinal (22.7 g = 80 % of the theory; the all-trans and 13-cis forms predominate) which can be converted into the all-trans form by isomerization and crystallization in accordance with methods disclosed in the literature.

EXAMPLE 21

Production of β-apo-12′-carotenal from 1-acetoxy-3-methyl-4-methoxy-1,3-butadiene 0.1 mole of chlorine is introduced at −20° C in the course of 15 minutes into a solution of 15.6 g (0.1 mole) of 1-acetoxy-3-methyl-4-methoxy-1,3-butadiene, 17.4 g (0.22 mole) of pyridine and 100 ml of methanol, and then solutions of 27 g (0.5 mole) of sodium methylate in 90 ml of methanol and 61.1 g (0.1 mole) retinyltriphenylphosphonium bromide in 130 ml of methanol are dripped in. The reaction mixture is then allowed to reach room temperature and acidified (to pH 2) with 2N aqueous sulfuric acid. Then 150 ml of water and 200 ml of heptane ia added, the whole is heated to 70° C, and the upper phase is separated at this temperature and washed with 200 ml of 60% aqueous methanol and 200 ml of water. The heptane is distilled off in a rotational evaporator. 24.8 g (71% of the theory) of β-apo-12′-carotenal is obtained in the form of a red oil (mixture of all-trans and 13-cis forms).

What we claimed is:

1. Substituted methyl-1-acetoxy-1,3-butadienes of the formula I

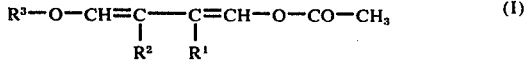

in which $R^1$ and $R^2$ are different and denote hydrogen or methyl and $R^3$ denotes an alkyl radical of from 1 to 4 carbon atoms or phenyl.

2. A substituted butadiene as set forth in claim 1 wherein $R^3$ is phenyl.

3. A substituted butadiene as set forth in claim 1 wherein $R^1$ is hydrogen and $R^2$ is methyl.

4. A substituted butadiene as set forth in claim 3 wherein $R^3$ is an alkyl radical of 1 to 4 carbon atoms.

5. A substituted butadiene as set forth in claim 1 wherein $R^1$ is methyl and $R^2$ is hydrogen.

6. A substituted butadiene as set forth in claim 5 wherein $R^3$ is an alkyl radical of 1 to 4 carbon atoms.

7. A substituted butadiene as set forth in claim 5 wherein $R^3$ is phenyl.

* * * * *